United States Patent
HJ. Che Idris et al.

(10) Patent No.: US 9,839,662 B2
(45) Date of Patent: *Dec. 12, 2017

(54) COMPOSITION FOR USE IN THE PREVENTION AND TREATMENT OF CARDIOVASCULAR DISEASES

(71) Applicant: Malaysian Palm Oil Board, Kajang, Selangor (MY)

(72) Inventors: Hjh Che Anishas HJ. Che Idris, Selangor (MY); Nagendran Balasundram, Selangor (MY); Ravigadevi Sambanthamurthi, Selangor Darul Ehsan (MY); Yew Ai Tan, Kuala Lumpur (MY); Kalyana Sundram P. Manickam, Selangor Darul Ehsan (MY); Mohd Basri Wahid, Selangor Darul Ehsan (MY)

(73) Assignee: MALAYSIAN PALM OIL BOARD, Kajang, Selangor (MY)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,410

(22) Filed: Apr. 20, 2015

(65) Prior Publication Data

US 2015/0224162 A1   Aug. 13, 2015

Related U.S. Application Data

(62) Division of application No. 14/322,680, filed on Jul. 2, 2014, which is a division of application No. 13/321,314, filed as application No. PCT/MY2010/000081 on May 19, 2010, now Pat. No. 8,778,419.

(30) Foreign Application Priority Data

May 18, 2009   (MY) ................. PI20092024

(51) Int. Cl.
| | | |
|---|---|---|
| *A61K 36/889* | (2006.01) | |
| *A61K 31/355* | (2006.01) | |
| *A61K 31/192* | (2006.01) | |
| *A61K 31/353* | (2006.01) | |

(52) U.S. Cl.
CPC .......... *A61K 36/889* (2013.01); *A61K 31/192* (2013.01); *A61K 31/353* (2013.01); *A61K 31/355* (2013.01)

(58) Field of Classification Search
CPC .................................................. A61K 36/889
USPC ................................................. 424/727, 777
See application file for complete search history.

(56) References Cited

U.S. PATENT DOCUMENTS

| | | | |
|---|---|---|---|
| 6,054,128 A * | 4/2000 | Wakat ................. | A23L 1/30 424/439 |
| 8,778,419 B2 | 7/2014 | Hj. Che Idris | |
| 2003/0031740 A1* | 2/2003 | Sambanthamurthi et al. ............. | 424/777 |
| 2005/0249803 A1 | 11/2005 | Udell | |
| 2006/0003947 A1 | 1/2006 | Udell | |
| 2008/0044539 A1 | 2/2008 | Perlman et al. | |
| 2010/0160690 A1 | 6/2010 | Lopez Mas et al. | |
| 2010/0184868 A1 | 7/2010 | Lopez Mas et al. | |
| 2014/0342023 A1 | 11/2014 | Hj. Che Idris | |

FOREIGN PATENT DOCUMENTS

| | | |
|---|---|---|
| WO | WO 2006/132879 A2 | 12/2006 |
| WO | WO 2007/131106 A2 | 11/2007 |
| WO | WO 2008/127086 A1 | 10/2008 |
| WO | WO 2009/013596 A2 | 1/2009 |
| WO | WO 2009/014417 A2 | 1/2009 |
| WO | WO 2009/110782 A1 | 9/2009 |
| WO | WO 2009/146102 A1 | 12/2009 |

OTHER PUBLICATIONS

International Search Report dated Sep. 2, 2010 for International Application No. PCT/MY2010/000081, 4 pages.
Das S. et al., "Cardioprotection with Palm Tocotrienol: Antioxidant Activity of Tocotrienol is Linked with its Ability to Stabilize Proteosomes," American Journal of Physiology—Heart and Circulatory Physiology, 2005, vol. 289, pp. 361-367.
Abeywardena M. et al., "Polyphenol-Enriched Extract of Oil Palm Fronds (*Elaeis guineensis*) Promotes Vascular Relaxation Via Endothelium-Dependent Mechanisms" Asia Pacific Journal of Clinical Nutrition, 2002, vol. 11, pp. S467-S472.

* cited by examiner

*Primary Examiner* — Chris R Tate
*Assistant Examiner* — Deborah Davis
(74) *Attorney, Agent, or Firm* — Merchant & Gould P.C.

(57) ABSTRACT

The invention provides a composition the prevention and treatment of cardiovascular disease, wherein said composition compounds obtained from palm oil mill effluents, in particular from vegetative liquor from the milling of palm oil fruit.

14 Claims, 2 Drawing Sheets

COMPOSITION FOR USE IN THE PREVENTION AND TREATMENT OF CARDIOVASCULAR DISEASES

This application is a Divisional Application of U.S. patent application Ser. No. 14/322,680, filed 2 Jul. 2014, which is a Divisional Application of U.S. patent application Ser. No. 13/321,314, filed 19 Jan. 2012, which is a National Stage Application of PCT/MY2010/000081, filed 19 May 2010, which claims benefit of Ser. No. PI20092024, filed 18 May 2009 in Malaysia. To the extent appropriate, a claim of priority is made to each of the above disclosed applications.

FIELD OF INVENTION

The present invention relates to the use of a composition for the prevention and treatment of cardiovascular disease, in particular the invention relates to a composition obtained based on extracts obtained from palm oil effluent, comprising vitamin E, phenolic flavanoids and combinations thereof, for the preparation of a means for the prevention and treatment of cardiovascular disease, particularly atherosclerosis.

BACKGROUND OF INVENTION

Atherosclerosis is an exemplary of a cardiovascular disease (CVD) that requires life long management in both prevention and treatment. It is recently considered the leading cause of death in South East Asia which accounts for approximately 4 million fatal cases each year. This particular disease is characterized by the hardening and thickening the inner lining of an artery with deposits that consist of fatty substances, cholesterol, cellular waste products, calcium and fibrin. Consequently, if not treated, the buildup known as plaque or atheroma, which embedded the walls of arteries will eventually block the arteries, and is the main contributory factor for heart attack, chest pain or stroke.

The main carrier in relation to the occurrence of cholesterol and its main source of damaging accumulation and blockage as mentioned above in the arteries is low-density lipoproteins (LDL). Generally, LDL carries cholesterol to peripheral tissues and accordingly passes through the endothelium that causes further development of plaques and therefore forms arterial wall cholesterol. Conclusively, patients with high amount of LDL have significantly high risk of atherosclerosis.

From the above, and recognizing the fact that by reducing or lowering the amount of LDL in patients may significantly assist to reduce the occurrence of atherosclerosis, the development of scientifically validated medicaments and treatments have been primed over the years based on this vital factor.

Ongoing scientific advancements include several chemically developed drugs that inhibit or lower the production of cholesterol; such drugs for instance include statins; and pharmaceutical compositions. Alternative approaches at present also include the consumption of juices or substances containing high level of antioxidants, for instance the pomegranate juice. The presence of antioxidants can assist to neutralize free radical damage. Free radicals are highly reactive chemical substances that can damage cellular materials, and therefore causes major degenerative illnesses including cardiovascular disease and cancer.

Additionally, botanical or plant based compositions have also played a major role in providing effectual remedies in relation to cardiovascular disease.

The major constituents in plant extract having beneficial properties comprise of antioxidants which have been widely known for treatment and prevention of a range of cholesterol related disease, wherein examples of antioxidants in plants are phenolics acids and flavanoids. Other plant based components or minerals with astronomical medicinal benefits which may be extracted from plants include potassium, calcium and magnesium, wherein the said minerals are well recognized for preventing and managing disorders such as hypertension, cardiovascular disease, and diabetes.

Following the above, the use of natural plant extracts having antioxidant properties instead of synthetic antioxidants for treatment of cardiovascular disease is now gaining momentum.

An exemplary of an excellent source of two major phytochemicals namely vitamin E (tocopherols and tocotrienols) and carotenoids, both of which are fat soluble, is the oil palm fruit. Palm vitamin E has been reported to act as a potent biological antioxidant, protecting against oxidative stress and the atherosclerotic process.

It is the primary objective of the present invention to provide a composition for preparing a medicament for the treatment of a cardiovascular disease, based on plant extract.

It is further an objective of the present invention to provide a composition for preparing a safe medicament for the treatment of a cardiovascular disease, said composition containing palm oil phenolics and palm vitamin E. The potential benefit is to inhibit the formation of plaque and thus inhibit the development of atherosclerotic lesions.

SUMMARY OF INVENTION

Figure 1A:
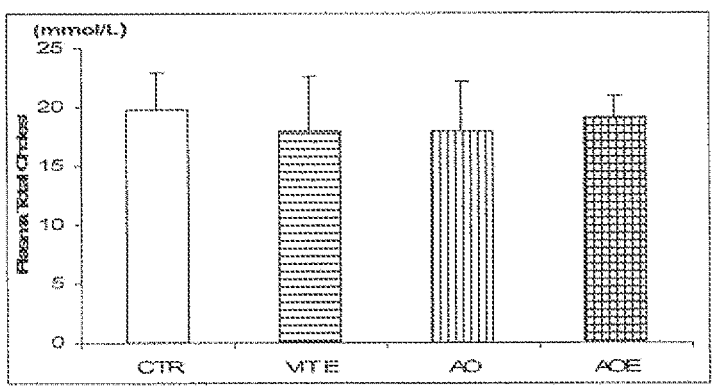
FIGS. 1A-D are the graphs showing the plasma lipid profiles of the rabbits in the four treatment groups.
Figure 1B:
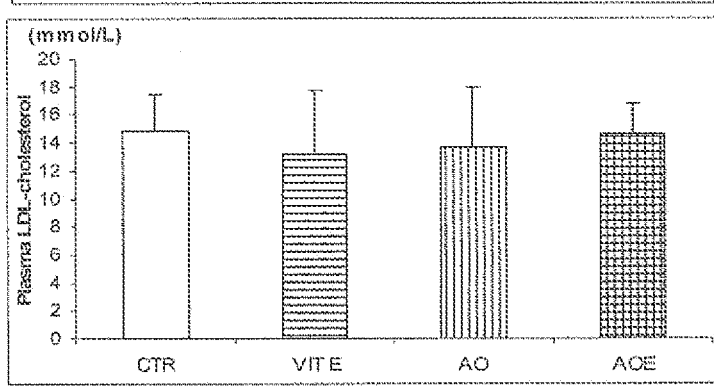
Figure 1C:
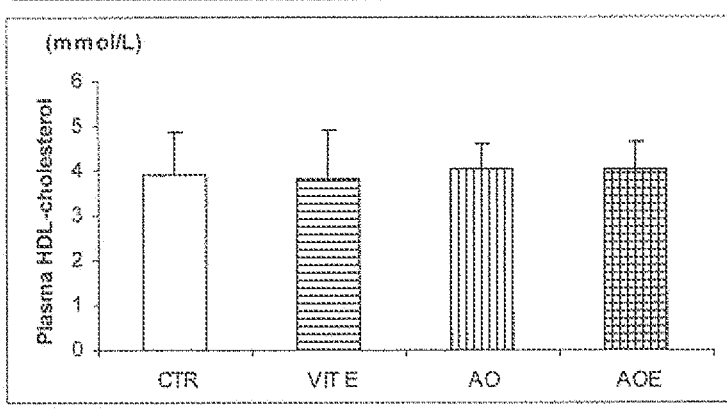
Figure 1D:
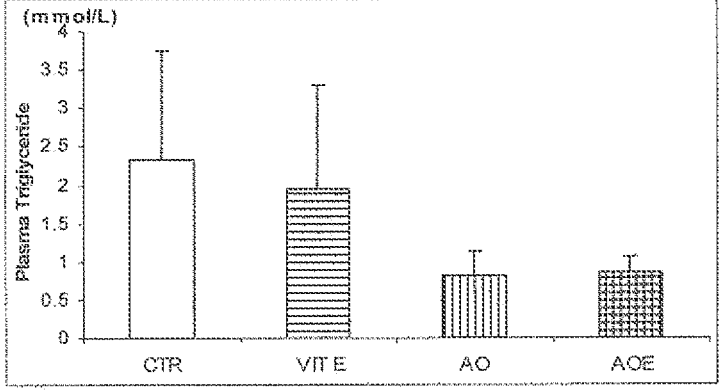

A composition for use in the preparation of a medicament for the prevention and treatment of cardiovascular diseases, said composition comprising components extracted from palm oil mill effluents.

In another aspect of the present invention, there is provided a composition for use in the prevention of cardiovascular diseases, said composition further comprising Vitamin E.

Further, the present invention relates to the use of therapeutically effective amount of a composition along with or without vitamin E, in the preparation of a medicament for preventing or inhibiting cardiovascular disease in an individual by administering to an individual in need thereof.

DETAILED DESCRIPTION

The present invention relates to the identification of excellent remedial effects for the prevention and treatment of cardiovascular disease, particularly atherosclerosis, based on palm phenolics and vitamin E, and thus the production of a composition on the same.

A water soluble crude extract rich in flavonoids and phenolic acids was successfully recovered from the vegetative liquor generated from the milling of oil palm fruits. The antioxidant activity of the palm phenolics extract in in vitro and in vive systems has been reported by Balasundram (2006). This extract has been tested and confirmed to have antioxidant properties and potent protective effects against cancer and atherosclerosis in animal and cell culture model systems.

The potential role of vitamin E to protect against free radical-mediated diseases has been the subject of many studies. There is now a growing interest in the nutritional and physiological properties of vitamin E in palm oil especially the tocotrienols. Epidemiological studies have linked dietary intake of vitamin E and other antioxidants with reduced risk of coronary heart disease (Rimm et al., 1993) and ischemic stroke (Bonner et al., 1995) and with a decrease in carotid artery thickness (Kritchevsky et al., 1995). Hodis et al. (1995) reported that antioxidant vitamins slowed the progress of coronary artery atherosclerosis, and Theriault et al. (2002) found that delta-tocotrienol was the most effective vitamin E for reducing the endothelial expression of adhesion molecules and adhesion on monocytes, thus reducing the risk of developing atherosclerosis.

The following examinations show that compared to the control diet, inclusion of palm vitamin E significantly reduced the extent of fibrous plaque in these animals. This finding is consistent with the observation by Kritchevsky et al. (2000) who reported that red palm oil containing both vitamin E and carotene, resulted in the least severe atherosclerotic lesions development compared to refined, bleached, deodorized (RBD) palm oil or randomized palm oil, and suggested that the carotenoids and vitamin E may protect against atherosclerosis. Similar effects was also observed from another study by Wilson et al. (1978), who found that addition of 1% (w/w) Vitamin E to the diet caused a marked reduction in aortic and coronary atherosclerosis in rabbits. The protective effect of vitamin E on cholesterol-induced atherosclerosis was also reported in an earlier study (Haiman, 1960). On the other hand, some researchers found that vitamin E had no effect on either plasma lipid parameters nor atherogenesis in the rabbit (Dam, 1994) while others reported that vitamin E improved some lipid parameters but did not inhibit the atherosclerotic plaque formation (Ismail et al., 2000).

Accordingly, in accordance to the preferred embodiments of the present invention, and based on the working example which will be described shortly, palm phenolics either on their own (AO) or in combination with vitamin E (AOE) has shown a significantly superior inhibitory effects on development of atherosclerotic lesions were observed in both the AO and AOE groups compared to the CTR and VIT E.

For the purpose of this invention, plasma antioxidant capacity was measured by two different methods i.e. the FRAP and ABTS$^{•+}$. Results obtained from the ABTS$^{•+}$ scavenging assay, showed no significant difference in all the four groups. Results from the FRAP assay also appeared to be not statistically significant, though plasma antioxidant capacity of the AO group and AOE group tended to be higher than that of the CTR group.

The methods and results obtained based on respective assays to determine the effectiveness of the said compounds in palm oil vegetation will be described herein.

BEST MODE FOR CARRYING OUT THE INVENTION

Working Examples

Materials and Methods
1. Animals, Diets and Experimental Design

Thirty-two male New Zealand White rabbits aged 4-5 months were randomly divided into 4 different treatment groups of 8 animals each. The animals were housed individually in stainless steel cages and maintained in a temperature controlled room (25° C.-28° C.) with a 12-hour daylight cycle. All animals were fed ad-libitum on an atherogenic diet for 100 days. Additionally, the animals were also provided vitamin E, palm phenolics or a combination thereof. The four experimental groups were classified as follows:
1. High Fat Atherogenic Diet–Control (CTR)
2. High Fat Atherogenic Diet+Vitamin E (VIT E)
3. High Fat Atherogenic Diet+Palm Phenolics (AO).
4. High Fat Atherogenic Diet+Vitamin E+Palm Phenolics (AOE).

The atherogenic diets were formulated as shown in Table 1. Diets contained 35% energy from fat.

TABLE 1

Composition of formulated rabbit atherogenic diet.

| Ingredients | g/kg diet |
| --- | --- |
| Casein | 250.0 |
| Corn starch | 200.0 |
| Dextrose | 193.0 |
| Cellulose | 150.0 |
| Mineral Mix | 40.0 |
| Vitamin Mix | 10.0 |
| Choline Bitartrate | 2.5 |
| DL-Methionine | 3.0 |
| Cholesterol | 1.5 |
| Dietary Fat | 150.0 |

The dietary fat used was designed to be atherogenic, and comprised: saturated fatty acids 67.1% (C12:0+C14:0=54.9%); monounsaturated fatty acids 15.7% (C18:1) and polyunsaturated fatty acids 12.0% (Table 2). The fatty acid composition of the dietary oil was determined as their methyl esters using gas chromatography (Sundram et al., 1997).

In diets of the VIT E and AOE group, palm vitamin E, rich in tocotrienols was used as the vitamin E source, and 1250 mg of this vitamin E was added to each kg of dietary fat. The final vitamin E content in the VIT E pellet diet was 237.0 mg/kg, whereas the base pellet diet (fed to CTR and AO groups) had 50 mg/kg vitamin E, primarily from the oil used in the diet formulation. Palm phenolics were provided to the AO and AOE group as their drinking fluid containing total phenolics at 1500 mg GAE/L. During the feeding trial, animals were continuously monitored for their food intake, water consumption and weight gain. The consumption of the palm phenolics of the AO and AOE group was measured over a 14-day continuous duration and was found to be approximately 150 mg GAE/day/animal.

TABLE 2

Content of major fatty acids (%) in the experimental diets.

| Carbon No. | Dietary Fat |
| --- | --- |
| SFA | 67.14 |
| 12:0 | 40.38 |
| 14:0 | 14.50 |
| 16:0 | 9.72 |
| 18:0 | 2.40 |
| 20:0 | 0.14 |
| PUFA | 12.02 |
| 18:2(n-6) | 11.88 |
| 18:3(n-3) | 0.14 |
| MUFA | 15.68 |
| 18:1(n-9) | 15.68 |

At the end of the feeding trial, all animals were sacrificed. Prior to sacrifice the animals were fasted overnight, anesthetized with a mixture of katemin and zoletil (0.1 mL/kg body weight) and 30 mL blood was drawn by heart puncture. Plasma was prepared by centrifugation at 3000 g for 20 minutes and stored at −80° C. until analyses. The animals were then overdosed with sodium pentobarbital before autopsy to remove various organs of interest such as liver, heart, lung and kidneys. The aorta system was carefully traced, dissected and cleaned of adherent adventitial tissue. The aorta was then cut open and preserved in 10% formalin solution before staining with oil Red-O for quantification of atherosclerotic lesions.

2. Biochemical Analyses and Measurements of Atherogenic Indices.

All laboratory analyses listed below are current and standard in most relevant laboratories.

Plasma Lipid Analysis

Plasma lipids (TC, triglycerides (TG), HDL-C), were analyzed using enzymatic assay kits (Roche Diagnostics GmbH, Mannheim, Germany) as per manufacturer's protocol on the clinical chemistry autoanalyzer, Roche/Hitachi 902.

Plasma Antioxidant Status

Plasma antioxidant status was measured by two methods; the 2,2'-azinobis(3-ethylbenzothiazoline) 6-sulfonic acid radical cation ($ABTS^{·+}$) decolorization assay and ferric reducing ability of plasma (FRAP).

The ability of rabbit plasma to scavenge the $ABTS^{·+}$ was measured using the method of Re et al. (1999) as adapted by Balasundram (2006). Essentially this assay measures the ability of antioxidants in the plasma to scavenge preformed $ABTS^{·+}$ produced by the oxidation of ABTS by potassium persulfate. The intensely coloured $ABTS^{·+}$ is relatively stable, but in the presence of an antioxidant, it is readily reduced to the colourless $ABTS^{·2-}$. The loss of absorbance at 734 nm after 6 min is taken as a measure of the $ABTS^{·+}$ scavenging activity. Standard $ABTS^{·+}$-scavenging curves were constructed using 6-hydroxy-2,5,7,8-tetramethylchroman-2-carboxylic acid (Trolox) and the $ABTS^{·+}$ scavenging capacity of the plasma is reported in terms of mg Trolox equivalents/mL (mg TE/mL).

The ferric reducing antioxidant power of plasma was determined using the method of Firuzi et al. (2005) as adapted by Balasundram (2006). The original FRAP assay was developed by Benzie & Strain (1996) as a test to measure the ferric reducing ability of plasma, i.e. the ability to reduce a ferric-2,4,6-tripyridyl-s-triazine ($Fe^{3+}$-TPTZ) to ferrous-2,4,6-tripyridyl-s-triazine ($Fe^{2+}$-TPTZ) via an electron transfer mechanism. This reduction resulted in the production of an intensely blue coloured reduced complex, with maximum absorption at 593 nm (Benzie & Strain, 1996).

Histopathological Examination

The aorta was stained with oil Red-O and quantification of the atherosclerotic lesions was undertaken by using an imaging analysis software (IDT-Solution). Lesions were categorized as shown in Table 3 below:

TABLE 3

Lesions characterization.

| Type of Lesions | Characteristics |
|---|---|
| Fibrous Plaque | Raised nodular lesions, continuous, intense red, white hard visible to naked eyes |
| Fatty Plaque | Raised distinct lesions, intensely stained red |
| Fatty streak | Lipid accumulation, stained light red |
| Lesion Free | No plaques or streaks |

Statistical Analyses

All data were analyzed using the analysis of variance (ANOVA) and the post hoc Tukey HSD to test differences between dietary groups/treatments. Differences were considered statistically significant at $p<0.05$.

Results

Mean body weights of the rabbits, prior to and at the end of the study, were not significantly different between all dietary groups after 100 days feeding (Table 4). This indicates that the experimental diet did not have any adverse outcomes on the normal growth curves of the experimental animals.

TABLE 4

Animal body weights after 100 days treatments.

|  | CTR | VIT E | AO | AOE |
|---|---|---|---|---|
| Initial wt (g) | 1871.43 ± 48.80 | 1857.14 ± 78.68 | 1860.97 ± 214.12 | 1822.27 ± 146.9 |
| Final wt (g) | 2229.43 ± 369.30 | 432.37 ± 171.39 | 2185.87 ± 752.94 | 2122.47 ± 375.10 | n = 8 animals/group
No significant differences between the treatments

At sacrifice, the weight of the liver, heart, lung and kidneys showed no significant difference between the treatment groups (VIT E, AO, AOE) and control group (Table 5).

TABLE 5

Effect of antioxidants on various organs of rabbits at autopsy

|  | CTR | VIT E | AO | AOE |
|---|---|---|---|---|
| Liver | 72.63 ± 11.34 | 61.83 ± 8.71 | 67.90 ± 12.63 | 64.46 ± 11.54 |
| Heart | 4.11 ± 0.83 | 4.45 ± 0.60 | 4.30 ± 0.71 | 4.15 ± 0.94 |
| Lung | 7.56 ± 1.63 | 7.20 ± 1.03 | 8.54 ± 1.57 | 7.26 ± 1.30 |
| Kidney | 9.60 ± 0.99 | 10.49 ± 1.59 | 11.72 ± 1.78 | 9.65 ± 2.42 | n = 8 animals/group
No significant differences between the treatments

The plasma lipid profiles of the rabbits in the four treatment groups are shown in FIG. 1A-D. These results do not show any significant difference between groups. It must be noted that these plasma samples were highly lipaemic. Nanji (1984) has reported that measurement of lipid profile of lipaemic samples is problematic as the lipaemia interferes with a variety of clinical chemistry analyses. Hence, further pretreatment of the samples was required to obtain more accurate results. Results were plotted as FIG. 1, whereby the effect of the treatments on plasma lipid profiles in rabbits can be observed. (A: Total cholesterol, B: LDL-cholesterol, C:

HDL-cholesterol, D: Triglyceride). Data are presented as means±sd from 8 animals/group.

Figure 2A:
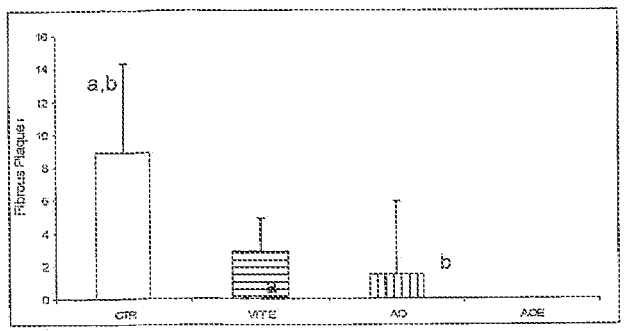
FIG. 2A-D are the graphs showing all rabbits in this experiment which were observed to have developed atherosclerotic lesions after feeding on the atherogenic diet for 100 days.
Figure 2B:
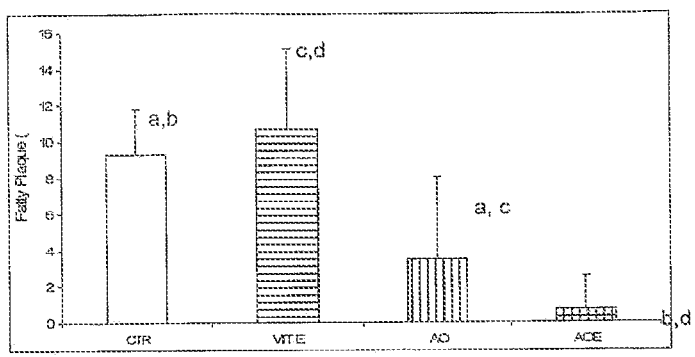
Figure 2C:
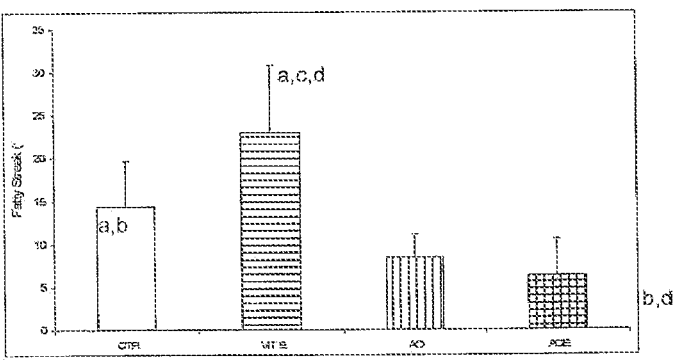
Figure 2D:
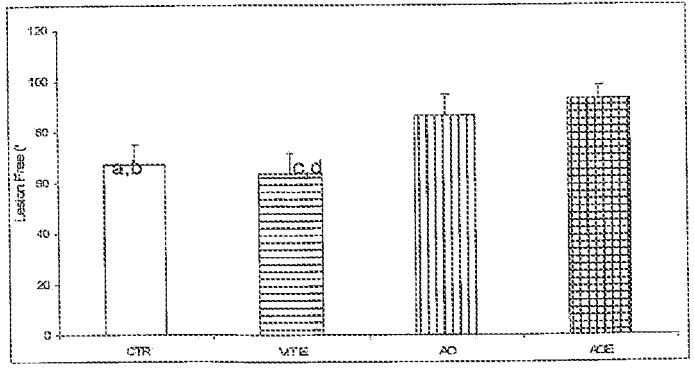

All rabbits in this experiment were observed to have developed atherosclerotic lesions after feeding on the atherogenic diet for 100 days (FIG. 2A-D). The CTR group had significantly higher fibrous plaque (FIG. 2A) score compared to the other three groups (VIT E, AO and AOE). In the AOE group, all animals did not show occurrence of fibrous plaques and this was significantly different (lower) compared to the CTR, the VIT E and AO groups. Fatty plaques (FIG. 2B) were significantly higher in both the CTR and VIT E groups compared to the AO and AOE treatments. In addition, the lowest fatty plaque score was apparent with the AOE treatment. Fatty streaks were highest in the VIT E treated animals followed by the CTR group (FIG. 2C). AO and AOE groups had significantly lower occurrence of fatty streaks compared to CTR and VIT E groups. Lesion free area (FIG. 2D), denoting the total area that was not altered morphologically (i.e. free of fatty streaks, fatty and fibrous plaques), was significantly higher following the AOE and AO treatments compared to the VIT E and CTR diets. This suggests protective effects due to AO and AOE treatments compared to the CTR and VIT E treatments, against occurrence of atherosclerosis.

FIG. 2 shows the development of atherosclerotic lesions (A: Fibrous Plaque, B: Fatty Plaque, C: Fatty Streaks, D: Lesion Free) after 100 days treatments. Values are means±SD (n=8 rats in each group) Means with common superscripts are significantly different (p<0.05).

To measure the antioxidant capacity of the rabbits plasma, two methods were used i.e. the ABTS$^{\cdot+}$ decolorization assay and FRAP assay. Though the FRAP results for AO (12.32±5.69 mg TE/mL) and the AOE group (10.53±4.84 mg TE/mL) were comparatively higher than that of the Control group (7.18±2.66 mg TE/mL), the differences were not statistically significant (Table 6). Similarly, there were no significant differences in the plasma ABTS$^{\cdot+}$ scavenging capacity of all the four groups. The use of two methods for measurement of antioxidant activity was based on the suggestion by Frankel & Meyer (2000) and Verhagen et al. (2003) on the need to evaluate antioxidant activity by using different methods. These two methods were chosen as they are amongst those most commonly used to measure the antioxidant capacity due to their rapidity of analysis, ease of use and high sensitivity (Maisuthisakul et al., 2007).

TABLE 6

Effect of the treatments on the antioxidant capacity in the rabbit plasma

|  | CTR | VIT E | AO | AOE |
|---|---|---|---|---|
| FRAP | 7.18 ± 2.66 | 6.17 ± 1.15 | 12.32 ± 5.69 | 10.53 ± 4.84 |
| ABTS | 74.95 ± 6.75 | 77.14 ± 4.88 | 75.73 ± 4.84 | 76.39 ± 5.12 |

In this study, the AO and AOE groups given palm phenolics as their drinking fluid did not exhibit significant changes in their plasma lipid profile (TC, TG, LDL-C and HDL-C), though the HDL-C level was observed to be slightly higher (statistically not significant) than the CTR and VIT E groups. However, these animals (AO and AOE groups) had significantly reduced incidence of atherosclerosis (i.e. less fatty streaks and plaques) than the CTR and VIT E groups. Similar observation was also reported by Wang et al. (2005) that no significant changes were seen in plasma lipid parameters between the control and any of the experimental groups at the end of the 12 week feeding duration. These authors found that dealcoholized red wine containing known amounts of resveratrol suppressed atherosclerosis in hypercholesterolemic rabbits and concluded that the phythochemicals in red wine can suppress atherosclerosis without affecting plasma lipid levels. In another rabbit study, Chen et al. (2005) fed a high-cholesterol diet for 10 weeks to rabbits, supplemented with or without mulberry fruit extract at two different concentrations (i.e. either 0.5% or 1%), and showed a significant decreased in plasma TC, LDL and TG levels.

The effect of palm phenolics in this study in inhibiting the formation of fibrous plaque was obvious in both the AO and AOE groups compared to the CTR and VIT E group, suggesting that palm phenolics may potentially inhibit atherosclerosis. This finding is in agreement with the findings of Fuhrman et al. (2005), who reported that fresh grape powder attenuated atherosclerotic development by reducing macrophages uptake of oxidized LDL and reduced macrophages cholesterol accumulation in apolipoprotein E-deficient (E$^\circ$) mice. These authors found no changes in the lipid profiles of the E$^\circ$ mice. Similarly, although no changes were seen in plasma LDL-C or HDL-C upon feeding of red wine to E$^\circ$ mice, reduced progression of lesions was reported by Hayek et al. (1997). Other recent animals studies also reported that consumption of pomegranate juice by mice (Kaplan et al., 2001), grape extract by hamsters (Auger et al., 2004). Similarly, consumption red wine, dealcoholized wine and wine polyphenols was found to reduce atherosclerotic lesions in E$^\circ$ mice, hamsters and rabbits (Manach et al., 2005). These results therefore show that the phenolics from palm could be similarly protective against atherosclerosis tendencies.

The compound of this invention may be prepared independently, in dosage form as described above, and can also be prepared combined together as combination product.

The dosage form as used herein above includes any suitable vehicle for the administration of medications known in the pharmaceutical art, including, by way of example, capsules, tablets, syrups, elixirs and solutions for parenteral injection with specified ranges of drug concentrations.

These examples are not intended, however, to limit or restrict the scope of the invention in any way and should not be construed as providing conditions, parameters, reagents or starting materials which must be utilized exclusively in order to practice the present invention.

The invention claimed is:

1. A method for reducing the propensity of a subject who is on a high fat diet from developing fibrous plaques, said method comprising regularly administering to said subject an effective amount of a nutritional supplement comprising an extract from palm oil mill effluents,
    wherein said nutritional supplement comprises palm phenolics and flavonoids from an aqueous stream or vegetation liquor of said palm oil mill effluents, palm vitamin E, and a suitable carrier therefor, and wherein said nutritional supplement is administered so as to provide the palm vitamin E in an amount of about 1250 mg per kg of dietary fat consumed by the subject.

2. The method of claim 1, wherein said subject is an animal.

3. The method of claim 2, wherein said nutritional supplement is a veterinary nutritional supplement.

4. The method of claim 1 wherein said palm vitamin E comprises tocotrienol.

5. The method of claim 1, wherein said palm phenolics are present in an amount of 1500 mg GAE/liter of the extract.

6. The method of claim 1, wherein said nutritional supplement is a dietary supplement.

7. The method of claim 1, wherein said nutritional supplement is administered in a dosage form selected from the group consisting of capsules, tablets, syrups, elixirs, and solutions for parental injection.

8. A method for reducing the propensity of a subject who is on a high fat diet from developing atherosclerotic lesions, said method comprising regularly administering to said subject an effective amount of a nutritional supplement comprising an extract from palm oil mill effluents,
wherein said nutritional supplement comprises palm phenolics and flavonoids from an aqueous stream or vegetation liquor of said palm oil mill effluents, palm vitamin E, and a suitable carrier therefor, and wherein said nutritional supplement is administered so as to provide the palm vitamin E in an amount of about 1250 mg per kg of dietary fat consumed by the subject.

9. The method of claim 8, wherein said subject is an animal.

10. The method of claim 9, wherein said nutritional supplement is a veterinary nutritional supplement.

11. The method of claim 8 wherein said palm vitamin E comprises tocotrienol.

12. The method of claim 8, wherein said palm phenolics are present in an amount of 1500 mg GAE/liter of the extract.

13. The method of claim 8, wherein said nutritional supplement is a dietary supplement.

14. The method of claim 8, wherein said nutritional supplement is administered in a dosage form selected from the group consisting of capsules, tablets, syrups, elixirs, and solutions for parental injection.

* * * * *